United States Patent
Ramanathan et al.

[11] Patent Number: 5,276,187
[45] Date of Patent: Jan. 4, 1994

[54] KETOXIME CARBONATES AND PROCESS FOR THE SYNTHESIS OF KETOXIME CARBONATES GENERALLY

[75] Inventors: Halasya Ramanathan, Washington; Chempolil T. Mathew, Randolph, both of N.J.

[73] Assignee: AlliedSignal Inc., Morristown, N.J.

[21] Appl. No.: 749,099

[22] Filed: Aug. 23, 1991

[51] Int. Cl.$^5$ .................. C07C 251/62; A01N 47/40; A61K 31/15
[52] U.S. Cl. .................. 564/254; 504/306; 504/344; 514/640
[58] Field of Search .......... 564/254; 514/640; 504/306, 344

[56] References Cited

U.S. PATENT DOCUMENTS

| | | | |
|---|---|---|---|
| 3,117,987 | 1/1964 | Horrom | 564/254 |
| 3,933,846 | 1/1976 | Daum | 548/306 |

FOREIGN PATENT DOCUMENTS

| | | |
|---|---|---|
| 2209840 | 10/1972 | Fed. Rep. of Germany . |
| 2234816 | 1/1974 | Fed. Rep. of Germany . |
| 3442018 | 5/1985 | Fed. Rep. of Germany . |
| 0061263 | 4/1968 | German Democratic Rep. . |
| 0124115 | 4/1983 | Poland . |
| 963055 | 7/1964 | United Kingdom . |

OTHER PUBLICATIONS

Kostyanovskii et al. "New derivatives of hexafluoroacetoneoxime" Izu. Akad. Nauk SSSR, Sea. Khim (7) 1615-1619 cited in Chem. Abst. 1974 81(21) 1353872.
Majewski et al., "0,0'-Carbonylbis (2-chlorocyclohexanone oxime)", Pol. PL 124,115, Apr. 30, 1983 abst. in Chem. Abst. 102: 24180; (1985) Columbus OH.

Primary Examiner—Richard L. Raymond
Assistant Examiner—P. O'Sullivan
Attorney, Agent, or Firm—Darryl L. Webster; Colleen D. Szuch; Jay P. Friedenson

[57] ABSTRACT

This invention relates to novel ketoxime carbonates and a process for the synthesis of ketoxime carbonates generally. Ketoxime carbonates are useful in a variety of applications. They may be used for example as pesticides, pharmaceuticals, weed control agents and dye stuff intermediates.

12 Claims, No Drawings

KETOXIME CARBONATES AND PROCESS FOR THE SYNTHESIS OF KETOXIME CARBONATES GENERALLY

FIELD OF THE INVENTION

This invention relates to novel ketoxime carbonates and a process for the synthesis of ketoxime carbonates generally. Ketoxime carbonates are useful in a variety of applications. They may be used for example as pesticides, pharmaceuticals, weed control agents and dye stuff intermediates.

BACKGROUND OF THE INVENTION

This application is directed to novel ketoxime carbonates and a method of preparing ketoxime carbonates generally. The ketoxime carbonates of the invention represent valuable intermediates. The process for preparing these compounds provides a route for synthesis of previously unknown substances, substances which are not commercially available and provides an efficient route for the synthesis of materials that were previously only manufacturable with great difficultly. The ketoxime carbonates that may be prepared via this process may be used in one or more of the following Utilities: pesticides, herbicides, pharmaceuticals, as well as, special solvents and intermediates for dyestuffs. See, for example U.S. Pat. No. 3,933,846 to Daum which discloses generally the preparation of benzimidazol-2-yl-carbamic acid alkyl esters. The reference discloses a special embodiment in which a 2-aminobenzimidazole is reacted with a carbonate, like acetone oxime carbonate, and an alkanol to form benzimidazol-2-yl-carbamic acid alkyl esters which are useful as plant protection agents and particularly useful as fungicides and mite ovicides.

Currently, ketoxime carbonates are prepared by reacting a desired ketoxime with phosgene. See, R. G. Kostyanovskii et al., "New Derivatives of Hexafluoroacetone oxime", (Translated from Izvestiya Akademii Nauk SSSR, Seriya Khimicheskaya, No. 7, pp. 1615-1619, July, 1974), which discloses the preparation of hexafluoroacetone oxime carbonate by the reaction of hexafluoroacetone oxime with phosgene and pyridine in ether at 20° C. See also, East German patent 61,263 to Jumar et al. in which acetone oxime carbonate is prepared as a by-product in low yield in a process for preparing chloroformyl oximes by reacting a ketoxime with phosgene.

It is an object of this invention to provide new ketoxime carbonates.

It is another object of this invention to provide a novel method for the preparation of ketoxime carbonates.

It is another object of this invention to provide a method of preparing ketoxime carbonates in high yield.

SUMMARY OF THE INVENTION

The invention relates to novel ketoxime carbonates of the formula:

wherein $R_1$ and $R_2$ each have at least one carbon atom and may be the same or different aliphatic, alicyclic or aromatic radical or taken together may form a cyclic structure and wherein said radicals may be unsubstituted or substituted with other than primary or secondary amino groups, hydroxyl groups, carboxyl groups or any other group which will react with aromatic carbonate providing that both $R_1$ and $R_2$ are not $CH_3$ or $CF_3$; and to a novel method of preparing ketoxime carbonates, generally, comprising: reacting a desired ketoxime with a substituted or unsubstituted aromatic carbonate under anhydrous conditions.

The ketoxime carbonates of the invention may be used in one or more of the following utilities: pesticides, herbicides, pharmaceuticals, as well as, special solvents and intermediates for dyestuffs.

DETAILED DESCRIPTION OF THE INVENTION

In one embodiment of the invention, $R_1$ and $R_2$ are unsubstituted.

In a preferred embodiment of the invention, either $R_1$ or $R_2$ has at least two carbon atoms.

In a more preferred embodiment of the invention either, $R_1$ or $R_2$ has at least three carbon atoms.

In another more preferred embodiment of the invention, either $R_1$ or $R_2$ has at least four carbon atoms.

In a still more preferred embodiment of the invention, either $R_1$ or $R_2$ has at least two carbon atoms and both $R_1$ and $R_2$ are unsubstituted.

In another still more preferred embodiment of the invention, either $R_1$ or $R_2$ has at least three carbon atoms and both $R_1$ and $R_2$ are unsubstituted.

In another still more preferred embodiment of the invention, either $R_1$ or $R_2$ has at least four carbon atoms and both $R_1$ and $R_2$ are unsubstituted.

In a most preferred embodiment of the invention, the ketoxime carbonates of the invention are selected from the group consisting of acetophenone oxime carbonate, 2-heptanone oxime carbonate, 4-methyl-2-pentanone oxime carbonate, cyclohexanone oxime carbonate and 2-butanone oxime carbonate.

$R_1$ and $R_2$ should not be substituted with groups which react with aromatic carbonate. Examples of groups to be avoided include primary and secondary amino groups, hydroxyl groups and carboxyl groups. Preferably, when the radicals are substituted they are substituted with nitro, alkylthio, alkoxy, halide, ester, amide and tertiary amino groups and more preferably halide, alkoxy and alkylthio groups.

Applicants have also discovered a novel method of preparing ketoxime carbonates, generally, comprising: reacting a desired ketoxime with a substituted or unsubstituted aromatic carbonate under anhydrous conditions.

Most of the ketoximes used in the invention are commercially available. 2-heptanone oxime, 4-methyl-2-pentanone oxime, cyclohexanone oxime and 2-butanone oxime may be purchased, for example, from Allied-Signal Inc., of Morristown, N.J. Alternately, these ketoximes and all other desired ketoxime starting material including acetophenone oxime may be synthesized in accordance with U.S. Pat. No. 4,323,706 to Bonfield et al.

The carbonate source may be any substituted or unsubstituted aromatic carbonate including diphenyl carbonate and substituted diphenyl carbonates. The diphenyl carbonate may be substituted, for example, with nitro, alkoxy, halogen and alkyl groups. Of the substituted diphenyl carbonates, p-tolyl carbonate and p-nitrophenyl carbonate are preferred. Other suitable carbonates will readily occur to those skilled in the art. Diphenyl carbonate is the preferred carbonate.

Diphenyl carbonate is commercially available. It may be purchased, for example, from the Mobay Corporation of Pittsburgh, Pa. Alternately, diphenyl carbonate may be prepared by following the method outlined in Bischoff and von Hedenstroem, *Chem. Ber.* 35, 3434 (1902). Substituted diphenyl carbonates may be synthesized in accordance with the methods disclosed in the following references: A. Gomberg and H. R. Snow, *J.A.C.S.*, 47, 198 (1925) and D. Martin and S. Rackow, *Ber.*, 98, 3662 (1965).

The process of the invention is conducted under anhydrous conditions as the carbonates are readily hydrolysed in water under reaction conditions. For purposes of this invention, "anhydrous" shall mean that water shall not comprise more than 0.5 weight percent of the reaction mixture and preferably not more than 0.1 weight percent.

The stoichiometry of the reaction requires at least 2 moles of ketoxime per mole of aromatic carbonate. An excess of ketoxime (i.e., greater than two (2) moles of ketoxime per mole of aromatic carbonate) is recommended in order to expedite the reaction. Accordingly, preferably from about 2.05 to about 8 moles of ketoxime per mole of aromatic carbonate are utilized and more preferably about 4 moles of ketoxime per mole of aromatic carbonate are utilized. The reaction is generally shown below:

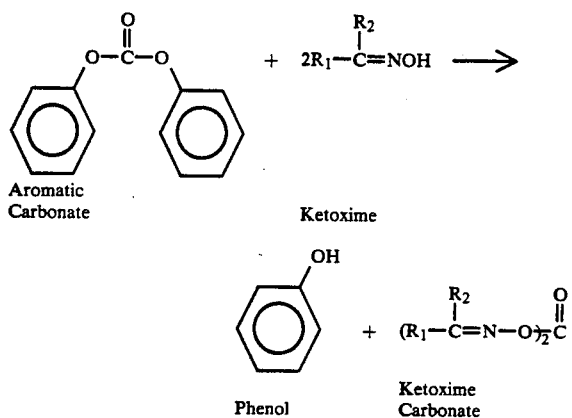

Thus, the process of the invention is preferably conducted in a single step. Specifically, a desired ketoxime is reacted with a substituted or unsubstituted aromatic carbonate under anhydrous conditions with at least two (2) moles of ketoxime per mole of aromatic carbonate to produce a desired ketoxime carbonate.

Although the stoichiometry requires at least 2 moles of ketoxime per mole of carbonate in order to convert directly to the desired ketoxime carbonate, the reaction may be conducted in two or more steps. For example, one (1) mole of a desired ketoxime may be reacted with a substituted or unsubstituted aromatic carbonate under anhydrous conditions then the intermediate product obtained from this step is reacted with a second mole of ketoxime to convert the intermediate to the desired ketoxime carbonate.

The reaction between ketoxime and aromatic carbonate may be conducted either neat (i.e., without solvent) or in the presence of a solvent. Suitable solvents include those compounds which are non-hydroxylic, contain no primary or secondary amino groups and have boiling points of at least about 85° C. Ethers, hydrocarbons, halogenated hydrocarbons, amides and substituted nitro compounds meeting the above criteria may be employed. Xylene, toluene, dioxane, chlorobenzene, pyridine, n-butyl ether, N,N-dimethyl formamide and triethylamine are preferred. However, other suitable solvents will readily occur to those skilled in the art.

Optionally, a catalyst may be employed in the reaction. Suitable catalysts include nitrogen containing heterocyclic compounds, as well as, aromatic, aliphatic and heterocyclic amines. Triethylamine and pyridine are preferred. Other suitable catalysts will readily occur to those skilled in the art. If a catalyst is used, preferably it should be used in an amount from about 0.1 to about 10 weight percent of the aromatic carbonate. See, Example 6.

The ketoxime/aromatic carbonate reaction mixture is heated at a temperature and for a time sufficient to produce the desired ketoxime carbonate. Generally, the reaction is heated at a temperature of from about 50° to about 200° C., more preferably from about 75° to about 135° C. and most preferably from about 90° to about 100° C. for a period of from about 1 minute to about 5 hours, more preferably from about 0.5 to about 3 hours and most preferably from about 1 to about 2 hours.

Because the reaction is reversible, it is preferred that the by-product produced, i.e., substituted or unsubstituted phenol, is continuously removed as it is produced. Thus, when the ketoxime starting material has a boiling point which is lower than the by-product phenol, following reaction of the ketoxime/aromatic carbonate mixture, (i.e., after heating at atmospheric pressure) reduced pressure is applied to remove the by-product phenol. When the ketoxime starting material has a boiling point which is higher than the by-product phenol, the entire reaction is preferably conducted at reduced pressure so that the by-product phenol is removed as it is formed.

EXAMPLE 1

Preparation of 2-proyano carbonate (carbonic acid bis-2-propanone oxime ester or acetone oxime carbonate). A solution of diphenyl carbonate (214 g/1.0 mole) and acetone oxime (365g/5.0 moles) in 214 ml toluene was purged with nitrogen and heated to about 110°–120° C. with efficient stirring in a one (1) liter 3-neck flask fitted with a thermometer and reflux condenser. The mixture was maintained at about 110°–120° C. for one (1) hour and cooled. Toluene, phenol and excess acetone oxime were removed under vacuum (70°–75° C. at 2 mm Hg) and the syrup obtained was cooled to room temperature to afford crystals. The crystals were filtered and washed with 100 ml petroleum ether to obtain 122 g of brownish crystals. The recrystallization of the crystals from anhydrous diethyl ether afforded colorless crystals (m.p. 74°–75° C.; Lit. 74°–74.5° C.). Yield: 70.9%. The identity of the product as acetone oxime carbonate was confirmed by IR, NMR (proton and carbon-13) and mass spectral analyses.

EXAMPLE 2

Preparation of acetophenone oxime carbonate.

A solution of diphenyl carbonate (5.35g/0.025 mole) and acetophenone oxime (13.5g/0.1 mole) in 25 ml toluene was placed in a 250 ml 3-neck flask fitted with a thermometer and reflux condenser. The mixture was heated to about 116° C. for one (1) hour under nitrogen. Toluene and all low-boiling components were removed under vacuum (70°-75° C. at 2 mm Hg). The syrup gave a solid upon standing. The solid was filtered and washed with 15 ml petroleum ether. The crude product was then dissolved in 20 ml ether and hexane was added to turbidity. After filtering and drying 7.2 g of colorless crystals appeared (m.p. 110°-112° C.). Yield: 97.3%. Confirmation of the compound as acetophenone oxime carbonate was obtained through IR and NMR spectral analyses.

EXAMPLE

Preparation of 2-hentanone oxime carbonate. A solution of 2-heptanone oxime (103.2g/0.8 mole) and diphenyl carbonate (42.8g/0.2 mole) in 50 ml toluene was heated with stirring in a 250 ml 3-neck flask fitted with a thermometer and reflux condenser. The mixture was heated to 130°-135° C. for one (1) hour under nitrogen and cooled. The mixture was rotovaped at 2 mm Hg at 90° C. to remove excess oxime, toluene and phenol. It gave 57.98g of a brownish oil which resisted crystallization. The product was then dissolved in 50 ml toluene, filtered through 35 g silica gel and eluted with 100 ml toluene. The toluene solution was evaporated to afford 54.87 g of light brown oil. Yield: 96.6%. The identity of the oily product as 2-heptanone oxime carbonate was confirmed by IR and NMR spectral analyses.

EXAMPLE 4

Preparation of 4-methyl-2-pentanone oxime carbonate. A solution of 4-methyl-2-pentanone oxime (46 g/0.4 mole) and diphenyl carbonate (21.4 g/0.1 mole) in 25 ml toluene was heated in a 250 ml 3-neck flask fitted with a thermometer and reflux condenser under nitrogen to 130°-135° C. for one (1) hour. The mixture was cooled and toluene, phenol and excess oxime were removed under vacuum (2 mm Hg and 90° C.) to afford 28.6 g of a dark brown syrup. The product was filtered through 20 g of silica gel using 125 ml toluene. The clear solution was distilled to remove solvent at 1 mm Hg and afforded 25.1 g of an orange-colored liquid. Yield: 98.04%. The liquid was identified as 4-methyl-2-pentanone oxime carbonate through IR and NMR (proton and carbon-13) analyses.

EXAMPLE 5

Preparation of 2-butanone oxime carbonate (carbonic acid bis-2-butanone Oxime), A solution of 2-butanone oxime (48.86g/0.56 mole) and diphenyl carbonate (39.9g/0.186 mole) in 70 ml N,N$^1$- dimethyl formamide was heated in a 250 ml 3-neck flask fitted with a thermometer and a reflux condenser under nitrogen. The mixture was heated to 125°-135° C. for one (1) hour. The mixture was cooled and solvent, phenol and excess oxime were removed by vacuum pump (2 mm Hg at 70° C.). 38.1 g of crude syrup were afforded. This syrup was filtered through a silica gel column (25 g) with 125 ml toluene as eluent. After evaporation and low vacuum pumping (1 mm Hg at 70° C.) to remove all volatiles, 36.1 g of a light orange syrup was obtained. Yield: 97%. The identity of the product as 2-butanone oxime carbonate was confirmed by IR and NMR (proton and carbon-13) analyses.

EXAMPLE

Preparation of 2-proyanone oxime carbonate utilizing triethylamine as catalyst. Acetone oxime (40.8 g/0.56 mole) was dissolved in 70 ml N,N-dimethylformamide. Diphenyl carbonate (39.9g/0.186 mole) was added to this mixture. Triethyl amine (0.8g) was added to the above mixture and heated to 120°-135° C. for one (1) hour. After removing the volatiles at 70°-90° C. and 2 mm Hg in a rotary evaporator a crude syrup was obtained. This crude syrup was crystallized from ether and produced 23 g of acetone carbonate (71% yield). Gas chromatographic analysis of the product revealed that the product was 90.9% pure.

EXAMPLE 7

Preparation of cyclohexanone oxime carbonate.

A solution of cyclohexanone oxime (46 g/0.4 mole) and diphenyl carbonate (21.4 g/0.1 mole) in toluene (25 g) was heated with stirring and maintained at 112° C. for 1 hour and 30 minutes. Phenol and excess oxime were then distilled off under vacuum (80°-110° C. at 7 mm/Hg. The residual brown viscous liquid weighed 27.2 g. NMR ($^1$H and C$^{13}$) and IR spectra were in agreement with the desired compound. The purity of the product was found to be —90% from the integration of $^1$HNMR Spectrum, the impurities being cyclohexanone oxime and phenol.

What is claimed is:

1. Ketoxime carbonates of the formula:

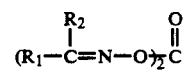

wherein either $R_1$ or $R_2$ has at least four carbon atoms and may be the same or different aliphatic, alicyclic or aromatic radical or taken together may form a cyclic structure and wherein said radicals may be substituted with nitro, alkylthio, alkoxy, halide, ester, amide and tertiary amino groups providing that when $R_1$ and $R_2$ are both alkyl or aromatic radicals or a mixture of alkyl and aromatic radicals they are substituted and said substitution is selected from the group consisting of nitro, alkylthio, alkoxy, halide, ester, amide and tertiary amino groups.

2. The alicyclic ketoxime carbonates of claim 1 wherein $R_1$ and $R_2$ are unsubstituted.

3. The cyclic ketoxime carbonates of claim 1 wherein $R_1$ and $R_2$ are unsubstituted.

4. The ketoxime carbonates of claim 1 wherein $R_1$ and/or $R_2$ are substituted with groups selected from the group consisting of nitro, alkylthio, alkoxy, halide, tertiary amino, ester and amide.

5. The ketoxime carbonates of claim 3 wherein $R_1$ and/or $R_2$ are substituted with groups selected from the group consisting of nitro, alkylthio, alkoxy, halide, tertiary amino, ester and amide.

6. The ketoxime carbonates of claim 4 wherein $R_1$ and/or $R_2$ are substituted with groups selected from the group consisting of alkylthio, alkoxy and halide.

7. The ketoxime carbonates of claim 1 wherein said ketoxime carbonate is cyclohexanone oxime carbonate.

8. The ketoxime carbonates of claim 1 wherein $R_1$ and $R_2$ are unsubstituted.

9. Ketoxime carbonates of the formula:

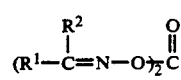

wherein either $R_1$ or $R_2$ has at least four carbons atoms and may be the same or different aliphatic, alicyclic or aromatic radical or taken together may form a cyclic structure and wherein said radicals may be substituted with nitro, alkylthio, alkoxy, halide, ester, amide and tertiary amino groups providing that when $R_1$ and $R_2$ are both alkyl or aromatic radicals or a mixture of alkyl and aromatic radicals they are substituted and said substitution is selected from the group consisting of nitro, alkylthio, alkoxy and halide, groups.

10. Ketoxime carbonates of the formula:

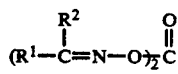

wherein either $R_1$ or $R_2$ has at least four carbons atoms and may be the same or different aliphatic, alicyclic or aromatic radical or taken together may form a cyclic structure and wherein said radicals may be substituted with nitro, alkylthio, alkoxy, halide, ester, amide and tertiary amino groups providing that when $R_1$ and $R_2$ are both alkyl or aromatic radicals or a mixture of alkyl and aromatic radicals they are substituted and said substitution is selected from the group consisting of nitro, alkylthio, alkoxy, halide, ester, amide and tertiary amino groups; with the proviso that said ketoxime is not bis(2-chlorocyclohexane)-carbonyl dioxime.

11. The ketoxime of claims 10 wherein $R_1$ and $R_2$ do not form a cycloalkyl structure having less than an 8 carbon ring.

12. The ketoxime of claims 10 wherein $R_1$ and $R_2$ do not form a cycloalkyl structure.

* * * * *